United States Patent [19]

Burkhead et al.

[11] Patent Number: 5,080,673
[45] Date of Patent: Jan. 14, 1992

[54] GLENOID PROSTHESIS AND METHOD OF USE

[75] Inventors: Wayne Z. Burkhead, Dallas; James L. Dale, Austin; Brian D. Burkinshaw, Pflugerville, all of Tex.

[73] Assignee: Intermedics Orthopedics, Inc., Austin, Tex.

[21] Appl. No.: 597,963

[22] Filed: Oct. 15, 1990

Related U.S. Application Data

[62] Division of Ser. No. 151,715, Feb. 3, 1988, Pat. No. 4,964,865.

[51] Int. Cl.$^5$ .............................................. A61F 00/00
[52] U.S. Cl. ................................................ 623/19
[58] Field of Search .................. 623/16, 18, 19, 20, 623/22, 23, 66

[56] References Cited

U.S. PATENT DOCUMENTS

| D. 285,969 | 9/1986 | Kinnett | 623/19 |
|---|---|---|---|
| 4,944,757 | 7/1990 | Martinez | 623/20 |
| 4,959,072 | 9/1990 | Morscher et al. | 623/16 |
| 4,990,161 | 2/1991 | Kampner | 623/20 |

FOREIGN PATENT DOCUMENTS

| 2910627 | 9/1980 | Fed. Rep. of Germany | 623/16 |
|---|---|---|---|
| 3535112 | 4/1987 | Fed. Rep. of Germany | 623/20 |
| 2541890 | 9/1984 | France | 623/19 |

Primary Examiner—David J. Isabella
Attorney, Agent, or Firm—John R. Merkling

[57] ABSTRACT

A glenoid prosthesis and method for affixing the same to a resected portion of a glenoid cavity on the head of the scapula. Th glenoid prosthesis has a lateral surface for articulating with the humeral head and a flat medial surface which engages a flat surface resected from the glenoid cavity. In a first embodiment, a pair of pegs extend medially from the flat medial surface of the glenoid prosthesis which are positioned in a pair of holes and the mating flat surfaces and pegs and holes are bonded with cement. The flat mating surfaces resist rocking under applied superior-inferior loading. Resection of the bone is simplified by providing a flat resected surface and holes drilled substantially perpendicular thereto. Preferably, grooves are provided in the pegs to provide an increased area for bonding, and preferably the grooves are graduated in depth to provide greater strength at the proximal end of the pegs where the highest stresses occur. In a second embodiment, the glenoid component consists of a metal base and plastic insert, wherein snap-fit locking means are provided for attaching the insert to the base and a central boss and screw fixation of the base to the bone provides stability and allows reconstruction with bone grafts.

9 Claims, 6 Drawing Sheets

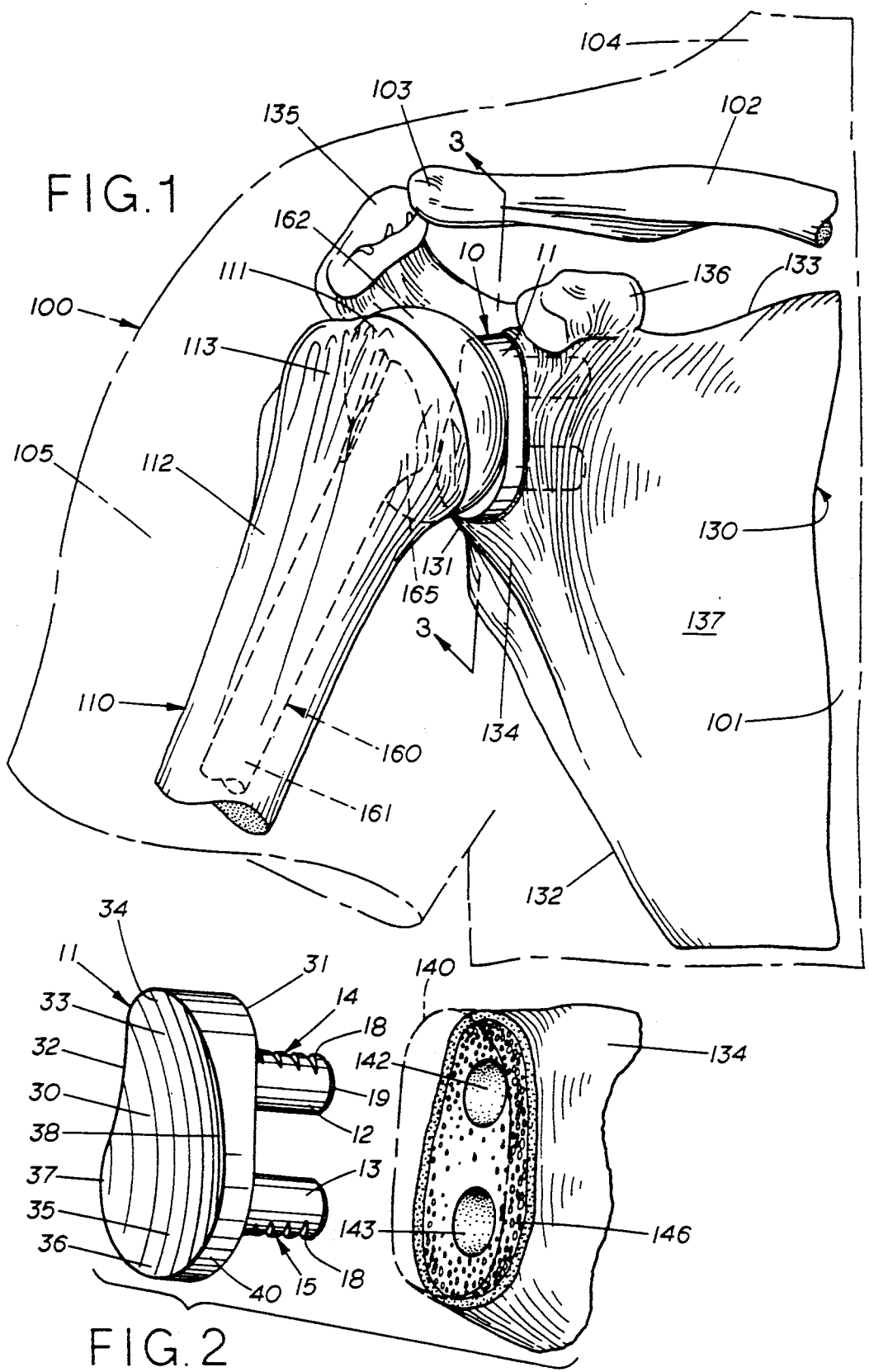

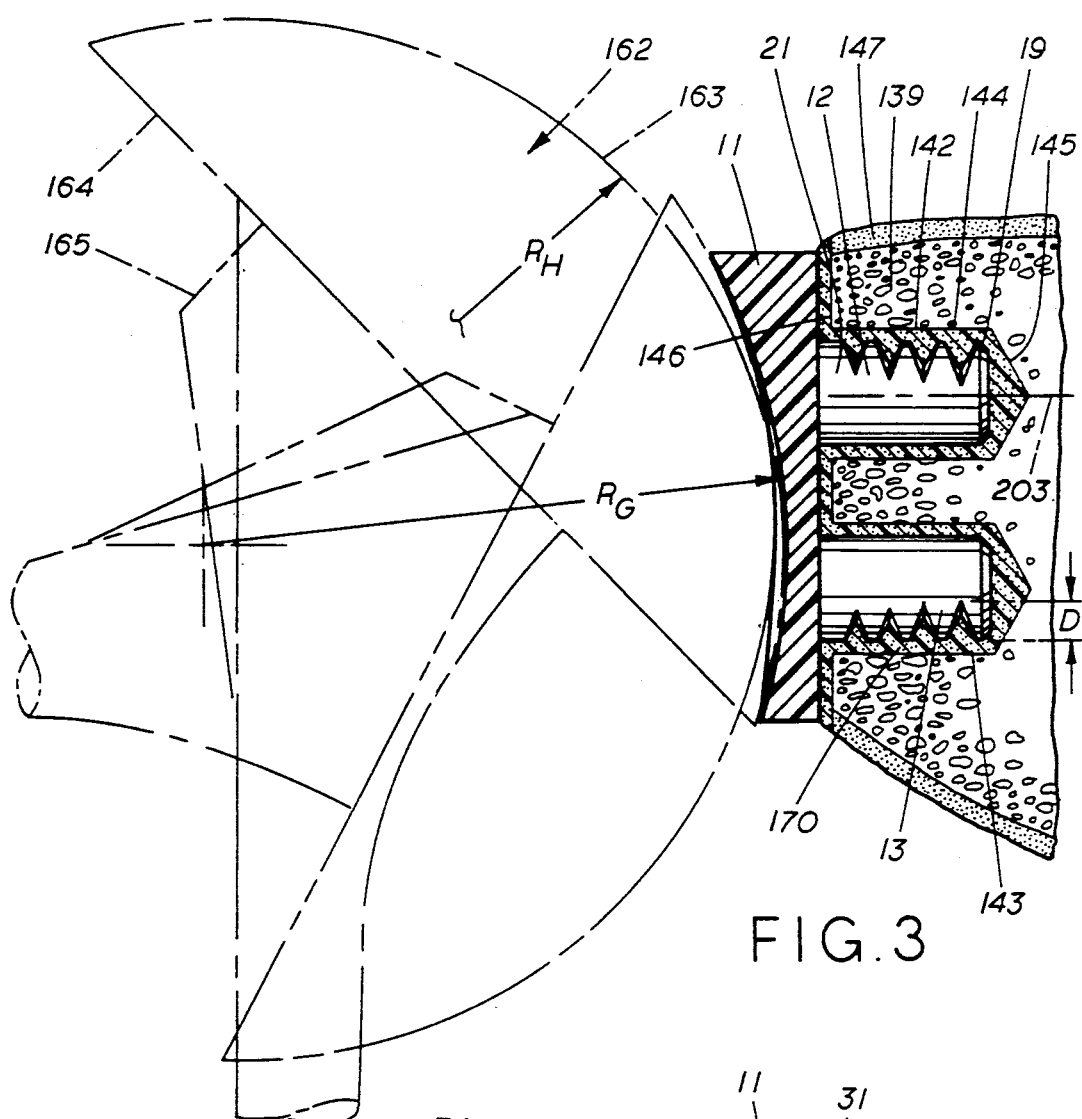

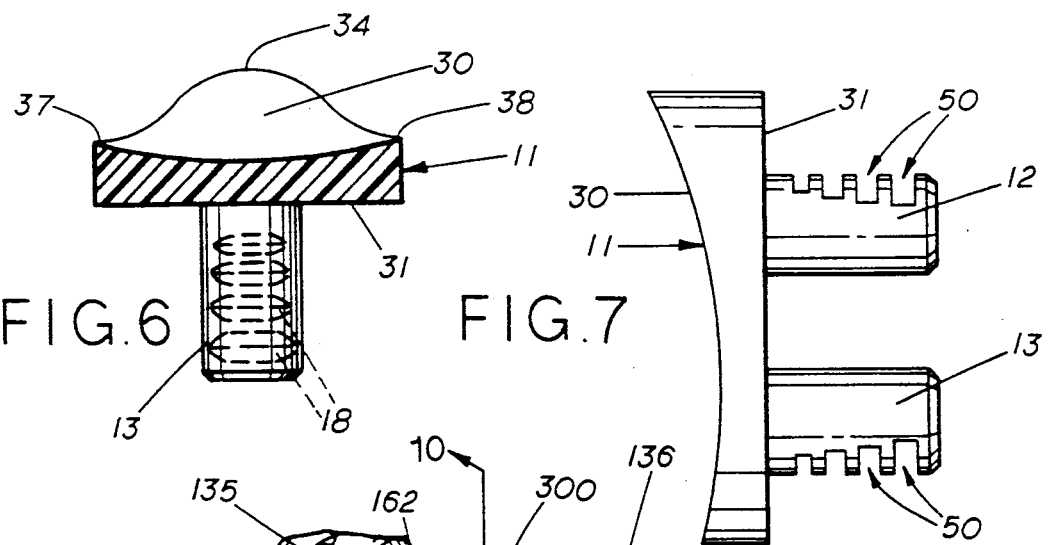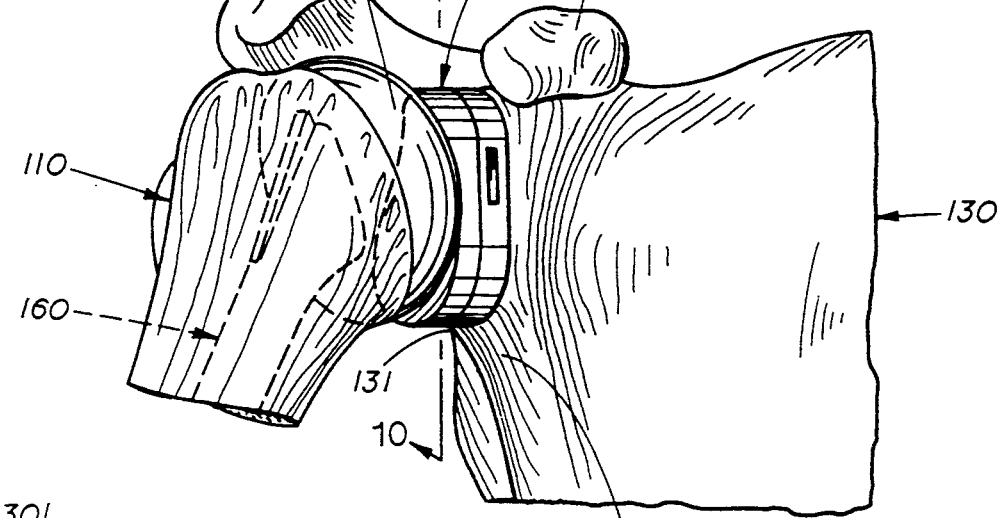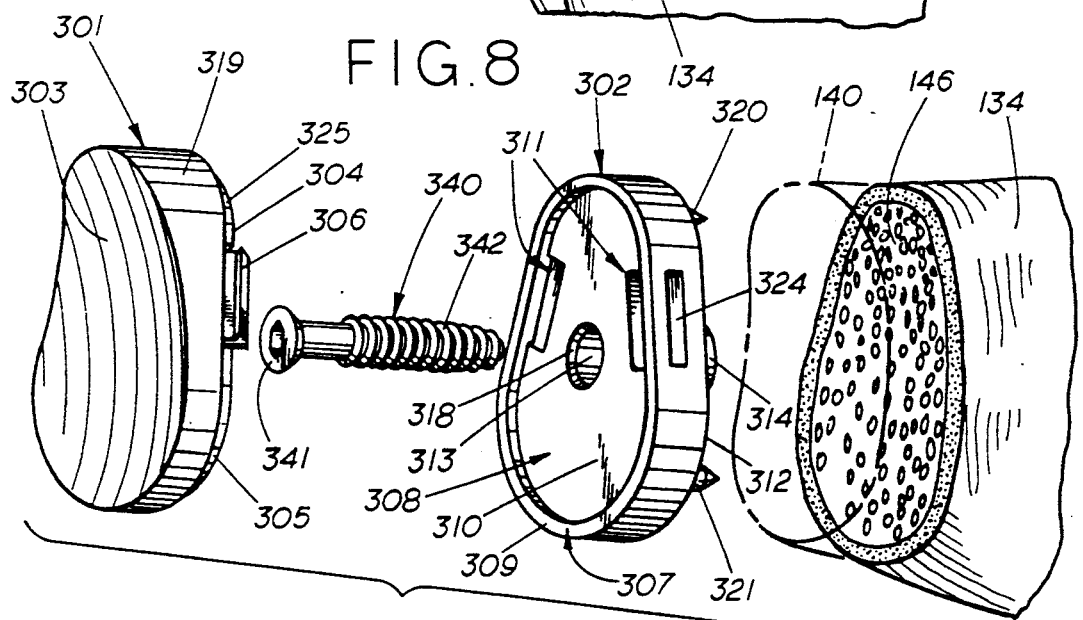

GLENOID PROSTHESIS AND METHOD OF USE

This is a divisional of copending application Ser. No. 07/151,715 filed on Feb. 3, 1988 now U.S. Pat. No. 4,964,865.

BACKGROUND OF THE INVENTION

This invention concerns a prosthesis for resurfacing the glenoid cavity of the shoulder and to a method of attaching the same which provides improved fixation of the prosthesis to the bone.

The glenoid cavity is located on the upper external border of the scapula between the acromion process and the coracoid process, on a bony formation known as the scapula head. The glenoid cavity is a shallow, pear-shaped, articular surface whose longest diameter is from above downward, and its direction outward and forward. It is broader below than above, and at its apex is a slight impression, the supra-glenoid tubercle, to which is attached the long tendon of the biceps muscle. The cavity is covered with cartilage and its margins, slightly raised, give attachment to a fibro-cartilaginous structure, the glenoid ligament, by which its cavity is deepened.

The glenoid cavity articulates with a large, rounded head at the proximal end of the humerus, or upper arm-bone. The head is nearly hemispherical in form and is directed upward, inward, and a little backward. Its surface is smooth and coated with cartilage.

There are at least four types of forces applied to the glenoid cavity which should be accounted for in designing a glenoid prosthesis.

First, there is straight compression loading which occurs, for example, when a person is standing with one side facing the wall and his arm straight out and he is leaning on the wall with his arm. This generates a compressive load which is transmitted straight into the humeral glenoid joint. The glenoid joint is designed to readily accomodate this straight compression loading.

Second, is a rotational shear loading which would occur, for example, when a person makes circles with his arms next to his body. This shear loading is generally of lesser magnitude.

Third, superior loading of the glenoid occurs, for example, when a person sits in his chair and puts his hands on the arm rests and pushes down to assist in getting up out of the chair. A superior loading force is applied to the superior end of the glenoid cavity which creates a moment load on the inferior end of the glenoid cavity.

Fourth, an anterior-to-posterior loading occurs, for example, when a person is sitting at a desk and pushes away from the desk with his arms.

The known glenoid prosthesis designs fail to accomodate one or more of these forces to the same extent as the glenoid prosthesis of this invention.

For example, the Neer II Total Shoulder System has a glenoid resurfacing component made of ultra-high molecular weight polyethylene (UHMWPE) having a concave lateral articulating surface and a convex medial surface with longitudinal grooves and a roughly triangularized fin projecting from the medial surface. The component is applied to the bone by using a right-angle burr to machine a trough into the center of the glenoid cavity about one inch long and about one ⅛ inch wide to accomodate the fin. The burr may be angled outwardly to widen the bottom of the fin cavity to prevent pullout of the fin once cement has solidified around the fin in the cavity. The fin further includes a central aperture and thickness variations, apparently to enhance the cement fixation. A metal-backed supporting shell is provided in an alternative embodiment having transverse grooves along the medial surface.

The Neer II glenoid component has been shown to loosen over time (i.e., detach from the bone) due to a superior-inferior rocking motion of the component. Superior loading applied to the superior margin of the glenoid component creates a moment load at the inferior end of the glenoid component causing the convex medial surface to rock along the superior-inferior longitudinal axis. The fin fails to prevent such rocking motion which causes either the cement to break down and the component to pull out, or causes the bone to break and the component to pull out.

Another known device, the DePuy shoulder prosthesis, has a glenoid component consisting of a plastic insert attached to a metal base. The medial surface of the base is cone shaped and four screw holes are provided through the base. The base is fixed to the bone by pushing the cone shaped base into a mating cavity resected from the glenoid cavity and by screwing four screws through holes in the base and into the bone. Again, in many cases, this design fails to resist the superior-inferior rocking motion which leads to a loosening of the component from the bone.

Another known device is the Richards-Cofield shoulder prosthesis, also having a glenoid component with a plastic insert and metal base. Again, the metal base has a curved medial surface and thus requires the use of a reamer to prepare a suitably curved mating surface in the glenoid cavity. The metal base plate further includes a central projection which is press-fit into the bone and a pair of superior-inferior screw holes with medially extending bosses which receive bone screws. The polyethylene insert is attached to the metal base by means of a slot. There have been problems with the insert dislocating from the metal base.

It is an objective of this invention to provide a glenoid prosthesis which can be fixed more securely to the bone so as to prevent loosening of the prosthesis or bone fracture under applied loads.

Another objective is to provide a glenoid prosthesis having an increased area for bone fixation.

A further objective is to provide an all plastic glenoid prosthesis which can be securely fixed to the bone with cement.

A further objective is to provide a metalbacked glenoid prosthesis which can be used to attach bone grafts.

A still further objective is to provide a glenoid prosthesis requiring a minimum number of steps to manufacture.

Another objective is to provide a new method for attaching a glenoid prosthesis resulting in improved fixation which resists loosening.

Yet another objective of the invention is to provide a method for attaching a glenoid component which can be performed more quickly and easily than the known methods.

SUMMARY OF THE INVENTION

This invention concerns a glenoid prosthesis of novel design and a new method for attaching the prosthesis to resist loosening and prevent bone fracture under applied loads.

In a first embodiment, the prosthesis consists of a glenoid component having a lateral surface for articulating with the humeral head and a flat medial surface, and at least two pegs projecting from the medial surface. Preferably, the prosthesis is an integral body formed of ultra-high molecular weight polyethylene (UHMWPE). The device is applied according to the method of the invention by resecting the glenoid cavity to provide a flat resected surface against which the flat medial surface of the glenoid component rests and by drilling holes into which the pegs are inserted. The mating flat surfaces and pegs are cemented in place.

The mating flat surfaces of the component and bone resist rocking caused by superior-inferior loading. Preferably, at least two spaced pegs are provided so that the component resists rotational loading. The spaced pegs also minimize the effect of superior-inferior loading and anterior-posterior loading. Preferably, grooves are provided on the pegs to increase the surface area for cement fixation. By providing grooves along only the outer faces of the pegs, the structural strength of the pegs is preserved and manufacture is simplified because the grooves can be machined in only a single operation. Preferably, the depth of the grooves decreases from the distal to the proximal end of the pegs and a proximal peg portion without grooves is provided adjacent the medial surface of the component. The greatest strength of the component is thus provided adjacent to the junction of the pegs and the medial surface of the component where the greatest shear stresses occur.

In a second embodiment of this invention, a metal-backed glenoid prosthesis is provided. The prosthesis includes a plastic insert having a lateral articulating surface for interacting with the humeral head, a flat medial surface having an indented edge which forms a raised medial portion, and a pair of snap-fit, outwardly projecting, L-shaped protrusions.

The prosthesis further includes a metal base whose lateral surface includes a recess sized to receive the medial portion of the insert and a pair of grooves to accept the snap lock protrusions and thus hold the insert securely on the base. The medial surface of the base is flat and mates with a flat resected bone surface. A central boss extends medially which is press fit or inserted into a predrilled hole in the bone and receives a bone screw for fixation to the bone. In addition, one or more posts or auxiliary screws are provided around the perimeter of the base to further stabilize the base against rocking and to prevent rotation of the base on the bone. The auxiliary screws may be angled to facilitate the attachment of bone grafts. A porous coating is provided on the medial surface of the base and on at least the proximal portion of the boss to promote bone ingrowth.

BRIEF DESCRIPTION OF THE DRAWINGS

FIG. 1 is an anterior schematic view of a right shoulder showing the head of a humeral prosthesis articulating with a first embodiment of the glenoid prosthesis of this invention; the prosthesis is an integral plastic body having two pegs with V-shaped teeth.

FIG. 2 is an exploded view of the glenoid prosthesis of FIG. 1 and the head of the scapula showing the resected glenoid cavity in broken lines and the peg holes for receiving the pegs of the glenoid prosthesis.

FIG. 3 is a sectional view of the glenoid prosthesis of FIG. 1 attached to the head of the scapula and showing the articulation of the humeral prosthetic head in broken lines.

FIG. 4 is a lateral plan view of the glenoid prosthesis of FIG. 1.

FIG. 5 is a medial plan view, in partial section, of the glenoid prosthesis of FIG. 1.

FIG. 6 is a sectional view of the glenoid prosthesis taken along the section lines 6—6 of FIG. 4.

FIG. 7 is an anterior plan view of a modified first embodiment of the glenoid prosthesis having rectangular teeth.

FIG. 8 is an anterior schematic view of a portion of a right shoulder showing the head of a humeral prosthesis articulating with a second embodiment of the glenoid prosthesis of this invention; the prosthesis includes a plastic insert and metal base with a screw fixation and four auxiliary posts.

FIG. 9 is an exploded view of the glenoid prosthesis of FIG. 8 and the head of the scapula showing the resected glenoid cavity in broken lines.

DETAILED DESCRIPTION OF THE PREFERRED EMBODIMENTS

Figure 10:
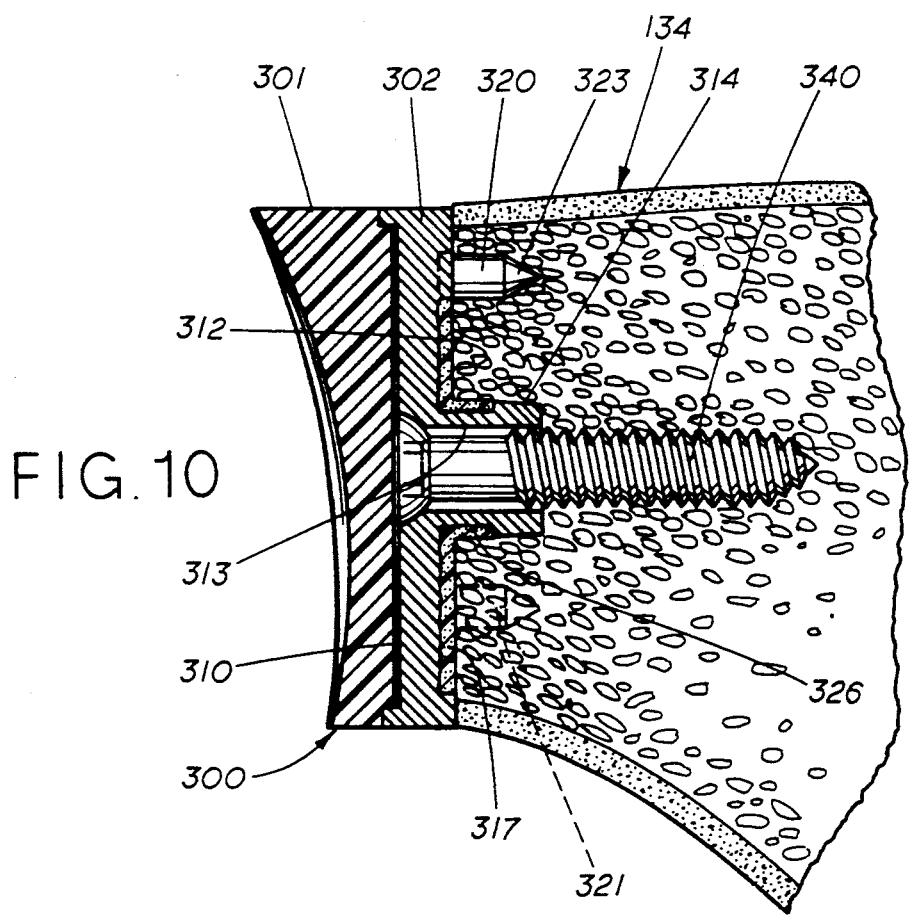
FIG. 10 is a sectional view of the glenoid prosthesis of FIG. 8 attached to the head of the scapula.
Figure 11:
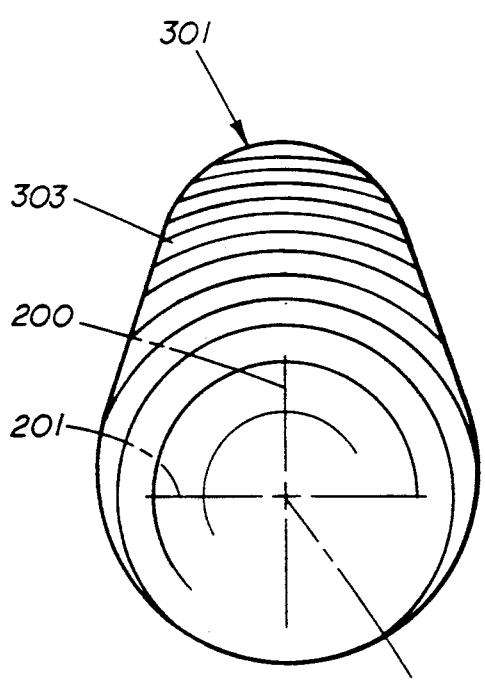
FIG. 11 is a lateral plan view of the plastic insert of the glenoid prosthesis of FIG. 8.
Figure 12:
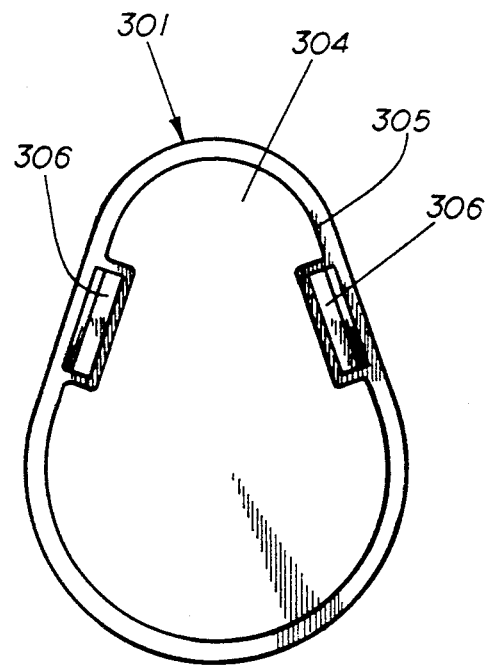
FIG. 12 is a medial plan view of the plastic insert of the glenoid prosthesis of FIG. 8.
Figures 13, 14, 15:
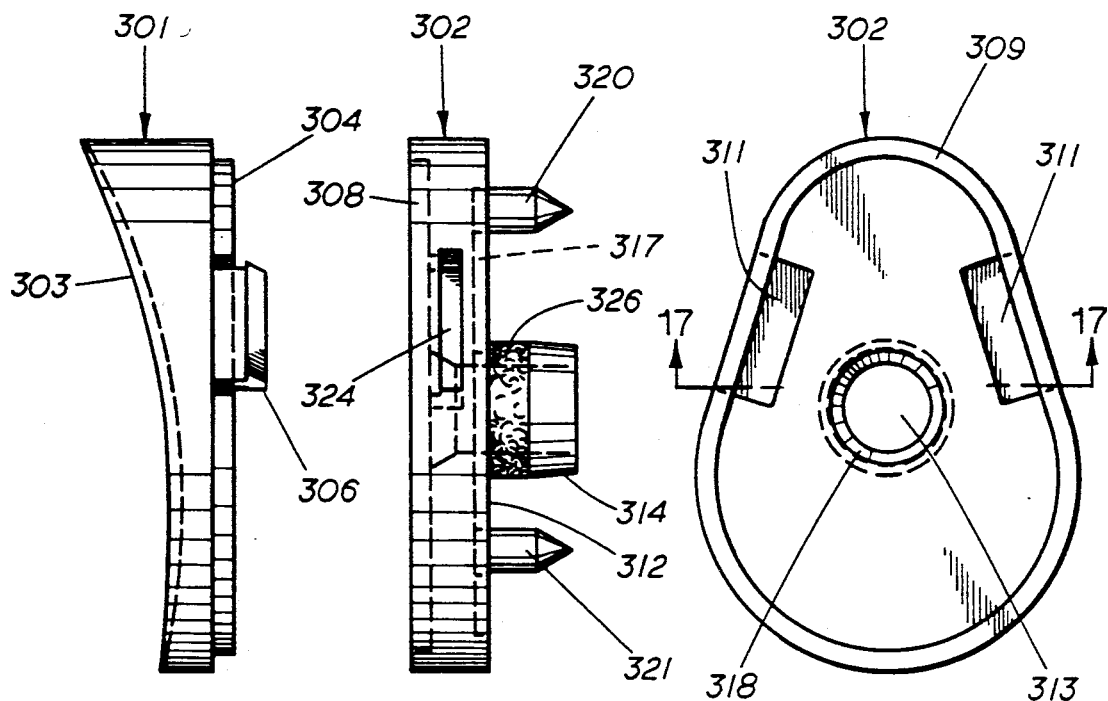
FIG. 13 is an anterior plan view of the plastic insert of the medial prosthesis of FIG. 8.
FIG. 14 is a anterior plan view of the metal base of the glenoid prosthesis of FIG. 8.
FIG. 15 is a lateral plan view of the metal base of the glenoid prosthesis of FIG. 8.
Figures 16, 17:
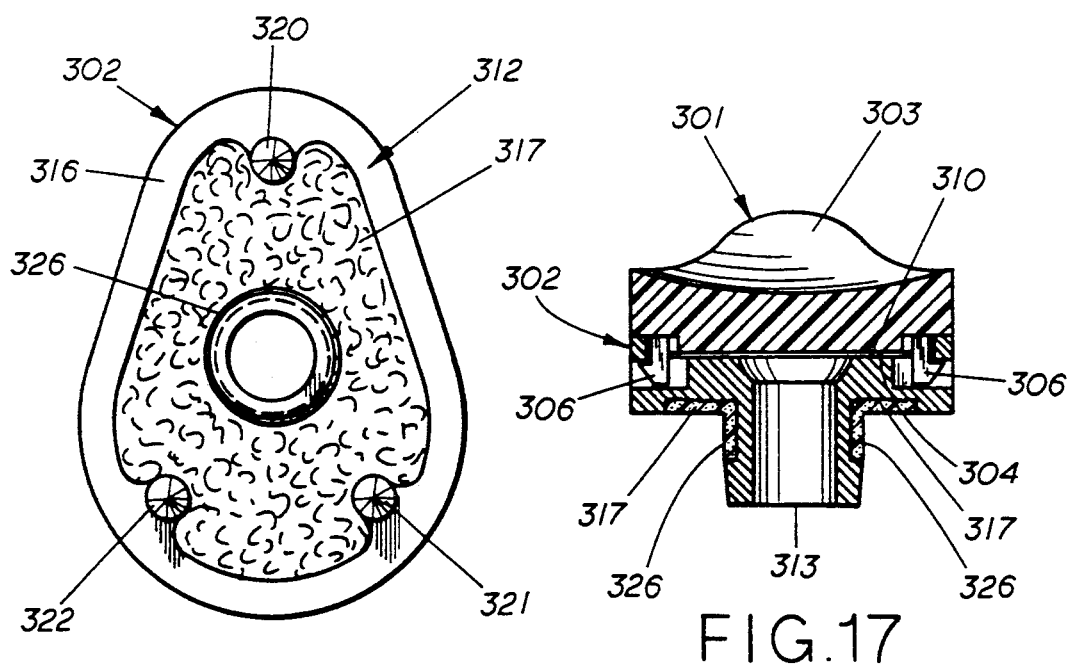
FIG. 16 is a medial plan view of the metal base of the glenoid prosthesis of FIG. 8.
FIG. 17 is a sectional view of the glenoid prosthesis taken along section lines 17-17 of FIG. 15.

FIG. 1 shows the anatomy of a human shoulder 100 with a first embodiment of the glenoid prosthesis 10 of this invention interacting with a head 162 of a humeral prosthesis 160. The anatomy shown includes an upper right arm 105 and the adjacent chest 101 and neck 104 areas. The glenoid prosthesis 10 is positioned in a resected portion of glenoid cavity 131 of scapula 130. The glenoid cavity 131 is located on the head 134 of the scapula between the external border 132 and upper border 133, and between the acromion process 135 and coracoid process 136. The head is lateral of the subscapular fossa 137. The acromial extremity 103 of clavicle 102 is positioned above the glenoid prosthesis 10.

The humeral prosthesis 160, which is made of a high-strength, light-weight metal such as a titanium alloy, is attached to the proximal end 113 of the humerus 110. The humeral prosthesis includes a stem 161 positioned in the medullary canal of the humerus shaft 112 and a spherical head 162 positioned adjacent head 111 of the humerus for articulation with a lateral articulating surface 30 of the glenoid prosthesis.

The glenoid prosthesis 10 is an integral plastic body, preferably made of ultra-high molecular weight polyethylene. It consists of a lateral glenoid component 11 having a lateral articulating surface 30, flat sidewalls 40, a flat medial surface 31, and a pair of pegs 12, 13 extending medially of the medial surface 31. The lateral component 11 has a pear-shaped perimeter 32 consisting of a broader inferior portion 35 and narrower superior portion 33. This shape approximates the aspect of the natural glenoid cavity. As a further approximation of the natural glenoid cavity, the component 11 has on its lateral side a relatively deep superior lip 34, a relatively shallow inferior lip 36, and posterior lip 37 and anterior lip 38 of equal depth and about the same depth as inferior lip 36. The lateral surface 30 thus comprises a substantially spherical surface with the center point of the sphere 202 located near the center of inferior portion 35, where longitudinal axis 200 intersects transverse axis 201 as shown in FIG. 4. The articulating surface 30 is symmetrical about the longitudinal center line 200, which extends between the superior 34 and inferior 36 ends of the component. Preferably, the component is about 1.00" to about 1.50" in the superior-inferior direction, about 0.75" to about 1.00" in the anterior-posterior direction, and about 0.30" to about 0.45" in the medial-lateral direction at its thickest point (i.e., superior margin).

The lateral articulating surface 30 of glenoid prosthesis 10 articulates with humeral head 162 as shown in FIG. 3. Humeral head 162 is substantially hemispherical, being of a radius $R_H$ which is less than the radius $R_G$ of the articulating surface 30. This allows substantially free sliding and rotational movement of head 162 on glenoid articulating surface 30. As shown in dashed lines, when the arm moves from a lowered to a raised position the head 162 slides and rotates on articulating surface 30 and the contact area changes to an inferior location from a superior location on the articulating surface 30. Head 162 has a smooth hemispherical outer surface 163 and a flat back surface 164, and is connected to stem 161 by a tapered proximal body portion 165.

The glenoid prosthesis 10 is fixed to the scapula 130 as shown in FIGS. 2 and 3. In the method of this invention, the defective articular cartilage and subchondral bone of scapula 130 is resected in an amount substantially equal to the height of sidewalls 40 of the prosthesis and a flat resected surface 146 is provided. Typically, about 2.0 mm to about 4.0 mm of bone is resected. This resection to provide flat resected surface 146 can be accomplished with a saw and is much easier and quicker to perform than prior art operations which require resection of curved surfaces into the scapula and/or preparation of a cavity within the glenoid cavity by means of a burr or like instrument. After resecting to flat surface 146, the surgeon then drills two peg holes 142, 143 into the cancellous tissue 139 of the remaining portion of scapula head 134. These holes are drilled substantially perpendicular to resected surface 146 by a drill bit to provide cylindrical sidewalls 144 and a conical end 145. The drill holes are made larger than the diameter of pegs 12, 13 in order to provide space for cement. Cement is inserted into the peg holes and applied on resected surface 146. Pegs 12, 13 are then inserted into holes 142, 143 and medial surface 131 is positioned adjacent resected surface 146, allowing the cement to form a continuous bond between the medial surface 31 and resected surface 146 and between pegs 12, 13 and peg holes 142, 143. A suitable cement is polymethylmethacrylate (PMMA). Typically, the pegs 12, 13 are about 4.0 mm to about 8.0 mm in diameter and about 10.0 mm to about 15.0 mm in length. The holes are about 2.0 mm wider in diameter and about 2.0 mm longer than the pegs.

Preferably, the pegs 12, 13 are positioned on the superior inferior centerline 200 an equal distance from the centerpoint 205 where anterior posterior centerline 204 crosses superior-inferior centerline 200 (see FIG. 5).

Preferably, a plurality of transverse grooves 18 are spaced along the longitudinal length (see longitudinal axis 203 in FIG. 3) of the pegs 12, 13 to provide an increased bonding area for the cement 160. These grooves may completely encircle each of the pegs or only a part thereof. In the preferred embodiment shown in FIGS. 1–6, V-shaped teeth 18 are provided only on the outer faces 14, 15 (i.e., facing the superior and anterior directions) of pegs 12, 13, respectively. By providing the teeth only on the outer faces, the teeth can be machined in a single operation with the component 11 rotating on a lathe. The teeth consist of two slanted sidewalls which form a V, as shown in FIGS. 2 and 3. Alternatively, the grooves may take any other shape such as rectangular teeth 50 shown in FIG. 7.

Preferably, the depth D of the teeth decreases from the distal (terminal) end to the proximal (adjacent medial surface 31) end of the peg. Thus, distal tooth 19 is cut more deeply into the peg than proximal tooth 20. In the example shown, the depth of the teeth varies at an angle of about 5° from the longitudinal center line 203 of the peg. In addition, the proximal tooth 20 is spaced from medial surface 31 to provide a proximal peg portion 21 which is uncut. By providing teeth of graduated depth and uncut proximal portion 21, the strength of the pegs is maximized adjacent medial surface 31 which is where the most severe stresses occur. Thus, the component is better able to resist these stresses.

The mating of flat medial surface 31 and flat resected surface 146 prevents movement between the prosthesis and bone, such as the superior-anterior rocking motion experienced by prior art prosthesis. The spaced pegs 12, 13 also resist the superior-anterior loading, as well as anterior-posterior loading. The glenoid component can accomodate straight compressive loads as well because of the flat resected surface which is substantially perpendicular to the applied compressive loads. Furthermore, the spaced pegs prevent possible rotations of the prosthesis in response to rotational shear forces.

In a second embodiment of the glenoid prosthesis of this invention, the prosthesis consists of a lateral plastic insert having a lateral articulating surface for articulation with the humeral head and a medial metal base having a central boss and screw and auxiliary post or screw fixation. The metal base and screw provides superior strength for fixation to the bone and the screw fixation allows for a method of firmly securing bone graft material beneath the prosthesis when additional reconstruction is warranted. The boss provides additional stability and resistance to shear loading. A pair of outwardly-facing snap-in locks provided on the anterior and posterior sides of the plastic insert fit within a pair of aligned grooves in the metal base for securing the insert and base together. This locking arrangement prevents any movement of the insert with respect to the base under shearing forces. A porous or textured coating is applied to the medial surface of the base and to the lateral portion of the boss exterior to promote bone ingrowth or cement attachment if cement is used.

Figure 18:
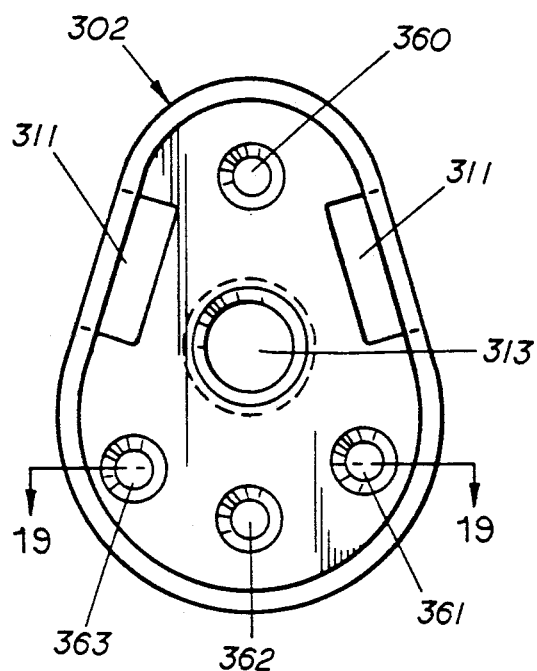
FIG. 18 is a lateral plan view of a modified second embodiment of the glenoid prosthesis having four auxiliary screw holes instead of four auxiliary posts.
Figure 19:
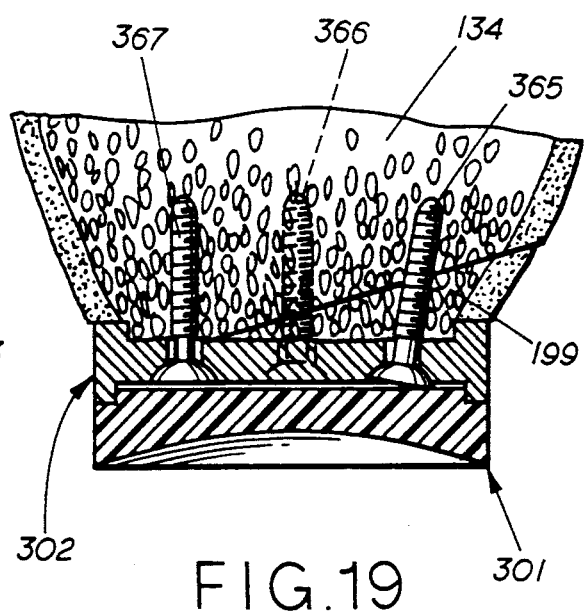
FIG. 19 is a sectional view of the glenoid prosthesis taken along section lines 19—19 of FIG. 18.

FIGS. 8–17 show a second embodiment of the glenoid prosthesis 300. FIGS. 18–19 show a modified second embodiment having four auxiliary screws for securing bone grafts, instead of four auxiliary posts.

The prosthesis 300 is positioned at the same location on the right scapula 130 as glenoid prosthesis 10 in FIG. 1. As shown in FIG. 9, the prosthesis 300 is positionable on the head of the scapula after removing resected bone 140 (shown in dashed lines) from glenoid cavity to form a flat resected surface 146.

Glenoid prosthesis 300 includes a plastic insert 301 having sidewalls 319 and a lateral articulating surface 303 identical to that of the prosthesis 10 in FIG. 2. However, in this embodiment the insert 301 fits within a recess 308 in metal base 302 for fixation to the bone. Insert 301 has a flat medial surface 304 with an indented edge 305 about the perimeter forming a raised medial portion 325 which is shaped and sized to fit within recess 308 defined by lip 309 and flat bottom wall 310 of the lateral surface 307 of base 302. A pair of snap-locks on the anterior and posterior sides of insert 301 are provided for attaching insert 301 to base 302. The snap-locks include resilient L shaped protrusions 306 extending medially and outwardly from the medial side of insert 301 which bend inwardly to snap-fit into L-shaped, outwardly facing grooves 311 on anterior-posterior sides of base 302. The L-shaped grooves 311 terminate in apertures 324 on the anterior and posterior sides of the base 302. It has been found that outwardly facing snap-locks provide a better attachment than inwardly facing snap-locks.

For fixation to the bone, base 302 has a central boss 314 extending medially from the flat medial surface 312. Boss 314 has a central bore 313 extending fully through the boss and base 302 for receiving bone screw 340. Base 302 further includes three medial posts 320, 321, 322 (or three screw holes in FIG. 18) extending medially of the flat medial surface 312 about the perimeter of the base for insertion into the bone to stabilize the base.

To place glenoid prosthesis 300 in the bone, the glenoid cavity is resected by a saw or similar device to form flat surface 146 on the head of the scapula. The medially extending posts 320-322 and boss 314 may be pushed into the cancellous tissue of scapula head 134 by applying a medially-directed force to bottom wall 310 of base 302. If the bone is sclerotic, holes for the posts and boss may be predrilled. Screw 340 is then inserted into bore 313 and screwed into the cancellous bone tissue until head 341 is flush with bottom wall 310. Insert 301 is then snap fit into base 302 by pushing L-shaped protrusions 306 into grooves 311 in the base 302.

The central boss 314 with screw fixation and the spaced posts 320-322 provide secure attachment of the prosthesis to the bone and prevent any rotation under applied shear forces. The mating engagment of medial protrusion 325 into recess 308, along with the L-shaped protrusions which snap-fit into grooves 311 provides secure attachment of insert 301 to base 302 which resists movement of the insert on the base under shear forces. By providing snap-locks on the insert which fit within lip 309 on the base and snap outwardly into groove 311, superior resistance to movement of the insert on base 302 is provided under applied shear forces. Alternatively, the protrusions and grooves 306, 311 could be positioned opposite one another on the anterior-posterior sides of the prosthesis or at any other position along the perimeter of the prosthesis to provide the same effect. In this case the anterior-posterior sides are selected because they provide the longest linear perimeter surfaces and it is easier provide the locks on a linear rather than a curved surface.

To further promote fixation of the prosthesis 300, a porous or textured coating is applied to the central portion 317 of medial surface 312 and to at least the lateral portion 326 of boss 314 to promote bone ingrowth and thus stable fixation. The porous coating on the boss should extend beyond the sclerotic bone and into the cancellous bone, since the sclerotic bone may not achieve optimum bone ingrowth. Viable, bleeding cancellous bone provides the best ingrowth matrix. A stable fixation ideally results in triaxial (x-y-z) stress transfer at the bone/prosthesis interface.

To further promote bone fixation, cement 170 may be applied between medial surface 312 of base 302 and resected surface 146 of the bone.

In the second embodiment of glenoid prosthesis 300 shown herein, insert 301 is a molded body of ultra high molecular weight polyethylene and base 302 is an integral body of titanium with a CPTi porous coating on surfaces 317 and 326. CPTi is commercially pure titanium and the coating is about 1.0 mm thick. Any textured surface or finish may be applied at 317 and 326, such as a spherical bead coating (e.g., U.S. Pat. No. 3,855,638), a fiber mesh coating (e.g., U.S. Pat. No. 3,906,550), a plasma spray textured coating (e.g., U.S. Pat. No. 3,605,123), or a ceramic porous aluminum coating (e.g., U.S. Pat. No. 4,179,485). Generally, the coating composition is based on substantially the same material as the metal base. However, a dissimilar coating may be used such as hydroxylapatite (e.g., U.S. Pat. No. 4,365,356). The base can be made of light-weight, high-strength alloys other than titanium, such as a cobalt-chrome alloy.

The central bore 313 of boss 314 accomodates a 6.5 mm titanium bone screw. The three pegs 320-322 are 3.2 mm in diameter. Instead of pegs 320-322, holes could be provided in base 302 for discretionary placement of one or more auxiliary 4.0 mm bone screws, as shown in FIGS. 18-19. Providing at least one post or screw in conjunction with central boss 314 and screw 340 prevents rotation of base 302 on the bone.

As shown in FIGS. 18-19, a further benefit of screw fixation is that it enables a surgeon to firmly secure bone graft material beneath the prosthesis when additional reconstruction is warranted. At least one, and preferably four auxiliary screw holes 360-363 are provided about the perimeter of the base which receive four auxiliary bone screws 364-367 for attaching bone chips or fragments between the scapula head 134 and base 302. As shown in FIG. 19, auxiliary screws 365 and 366 at the inferior end of base 302 pass through the graft chip 199 and into the scapula head 134. The position of the auxiliary screws may be varied and the screws may be angled for attaching a bone graft at any location. Generally, the anterior or posterior margin needs reconstruction and the auxiliary screws may be angled at 15° or 20° to pass through and attach the bone graft. In addition, the bone graft may be secured into position by wedging it between two or more of screw 340, posts 320-322, and auxiliary screws 364-367.

While certain preferred embodiments of the invention have hereinbefore been described, it will be appreciated that variations of the invention will be perceived by those skilled in the art. For example, the number, size, shape and positioning of the pegs, posts and screws may be varied, as well as the number, shape and size of grooves in the pegs. The materials and dimensions of the glenoid component may also be varied. These variations are nevertheless within the scope of the invention as defined by the claims appended hereto.

What is claimed is:

1. A method of attaching a glenoid prosthesis comprising:
   resecting at least a portion of the glenoid cavity on the head of the scapula to provide a flat resected surface;
   resecting at least one hole substantially perpendicular to the flat resected surface;
   positioning a glenoid component having a substantially flat medial surface and a peg means extending substantially pependicular thereto against the flat resected surface and into the hole, respectively; and
   bonding the medial surface to the resected surface and the peg means in the hole.

2. The method of claim 1, wherein the hole is resected by drilling.

3. A method of attaching a glenoid prosthesis comprising:
   resecting at least a portion of the glenoid cavity on the head of the scapula to provide a flat resected surface;
   positioning a glenoid component having a substantially flat medial surface and a medially extending boss by inserting the boss into the resected scapula head and positioning the flat medial surface against the flat resected surface; and
   screwing a bone screw through the boss and into the scapula head for attaching the component to the scapula head.

4. The method of claim 3, wherein the glenoid component includes a plastic insert and metal base and means for attaching the insert to the base, wherein the positioning step includes attaching the base to the scapula head prior to attaching the insert to the base.

5. The method of claim 3, wherein the glenoid component further includes an auxiliary peg means, and the method further comprising:
   inserting the auxiliary peg means into the resected scapula head.

6. The method of claim 5, wherein the boss and peg means are inserted into the scapula head by applying medially directed force against a lateral surface of the component to push the boss and peg means into the resected scapula head.

7. The method of claim 6, wherein the boss and peg means are inserted into the resected scapula head by predrilling holes into the scapula head and positioning the boss and peg means in the predrilled holes.

8. A method of attaching a glenoid prosthesis and a bone graft to the head of the scapula comprising:
   positioning a bone graft on the deteriorated head of a scapula to form a reconstructed surface;
   positioning a glenoid component having a medial surface, a medially extending boss with a bore and at least one auxiliary screw hole such that the boss is inserted into the scapula head and the medial surface is positioned against the reconstructed surface; and
   attaching the glenoid component and bone graft to the scapula head by inserting a bone screw through the boss and screwing the bone screw into the scapula and inserting an auxiliary bone screw through the auxiliary screw hole and screwing the auxiliary bone screw through the bone graft and into the scapula head.

9. The method cf claim 8, wherein the auxiliary bone screw is angled with respect to the reconstructed bone surface.

* * * * *